United States Patent
Afik (10) Patent No.: US 8,155,414 B2
(45) Date of Patent: Apr. 10, 2012

(54) DEVICE, SYSTEM AND METHOD OF IN-VIVO VARIX DETECTION

(75) Inventor: Daniel Shmuel Afik, Misgav (IL)

(73) Assignee: Given Imaging Ltd., Yoqneam (IL)

( * ) Notice: Subject to any disclaimer, the term of this patent is extended or adjusted under 35 U.S.C. 154(b) by 463 days.

(21) Appl. No.: 12/443,112

(22) PCT Filed: Sep. 25, 2007

(86) PCT No.: PCT/IL2007/001182
§ 371 (c)(1),
(2), (4) Date: Mar. 26, 2009

(87) PCT Pub. No.: WO2008/038278
PCT Pub. Date: Apr. 3, 2008

(65) Prior Publication Data
US 2010/0027858 A1  Feb. 4, 2010

Related U.S. Application Data (60) Provisional application No. 60/847,932, filed on Sep. 29, 2006.

(51) Int. Cl.
*G06K 9/00* (2006.01)
(52) U.S. Cl. ........................................................ 382/128
(58) Field of Classification Search ........... 382/128–134
See application file for complete search history.

(56) References Cited

U.S. PATENT DOCUMENTS

2004/0264754 A1  12/2004  Kleen et al.
2007/0078300 A1*  4/2007  Zinaty et al. .................. 600/102

* cited by examiner

*Primary Examiner* — David Mis
(74) *Attorney, Agent, or Firm* — Pearl Cohen Zedek Latzer, LLP (57) ABSTRACT

Devices, systems and methods of in-vivo varix detection. For example, a system may include a processor to automatically detect a varix in an in-vivo image. The processor may automatically identify a protrusion into a lumen of a gastro-intestinal tract. The processor may automatically identify substantially blue areas of the protrusion. The processor may generate an indication to a user that a varix was detected in an in-vivo image.

13 Claims, 4 Drawing Sheets

DEVICE, SYSTEM AND METHOD OF IN-VIVO VARIX DETECTION

CROSS-REFERENCE TO RELATED APPLICATIONS

This application is a National Phase Application of PCT International Application No. PCT/IL2007/001182, International Filing Date Sep. 25, 2007, claiming priority of U.S. Provisional Patent Application No. 60/847,932, filed Sep. 29, 2006, which is hereby incorporated by reference.

FIELD OF THE INVENTION

The present invention relates to the field of in-vivo sensing, for example, in-vivo imaging.

BACKGROUND OF THE INVENTION

Some in-vivo sensing systems may include an in-vivo imaging device able to acquire and transmit images, for example, of the gastro-intestinal (GI) tract while the in-vivo imaging device passes through the GI lumen.

Other devices, systems and methods for in-vivo sensing of passages or cavities within a body, and for sensing and gathering information (e.g., image information, pH information, temperature information, electrical impedance information, pressure information, etc.), are known in the art.

Some in-vivo imaging devices may acquire a large number of in-vivo images, for example, hundreds or thousands of in-vivo images, e.g., over a period of several hours. Accordingly, a relatively long time period may be required from a physician in order to view the acquired in-vivo images.

SUMMARY OF THE INVENTION

Some embodiments of the present invention may include, for example, devices, systems and methods of in-vivo varix detection In some embodiments, for example, a system may include a processor to automatically detect a varix in an in-vivo image, e.g., of the GI tract.

In some embodiments, for example, the in-vivo imaging device may be autonomous.

In some embodiments, for example, the in-vivo imaging device may include a swallowable capsule.

Embodiments of the invention may provide various other benefits and/or advantages.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements throughout the serial views.

DETAILED DESCRIPTION OF THE INVENTION

In the following detailed description, numerous specific details are set forth in order to provide a thorough understanding of the present invention. However, it will be understood by those skilled in the art that the present invention may be practiced without these specific details. In other instances, well-known methods, procedures, and components have not been described in detail so as not to obscure the present invention.

Although a portion of the discussion may relate to in-vivo imaging devices, systems, and methods, the present invention is not limited in this regard, and some embodiments of the present invention may be used in conjunction with various other in-vivo sensing devices, systems, and methods. For example, some embodiments of the invention may be used, for example, in conjunction with in-vivo sensing of pH, in-vivo sensing of temperature, in-vivo sensing of pressure, in-vivo sensing of electrical impedance, in-vivo detection of a substance or a material, in-vivo detection of a medical condition or a pathology, in-vivo acquisition or analysis of data, and/or various other in-vivo sensing devices, systems, and methods.

Some embodiments of the present invention are directed to a typically one time use or partially single use detection and/or analysis device. Some embodiments are directed to a typically swallowable in-vivo device that may passively or actively progress through a body lumen, e.g., the gastro-intestinal (GI) tract, for example, pushed along by natural peristalsis. Some embodiments are directed to in-vivo sensing devices that may be passed through other body lumens, for example, through blood vessels, the reproductive tract, or the like. The in-vivo device may be, for example, a sensing device, an imaging device, a diagnostic device, a detection device, an analysis device, a therapeutic device, or a combination thereof. In some embodiments, the in-vivo device may include an image sensor or an imager. Other sensors may be included, for example, a pH sensor, a temperature sensor, a pressure sensor, sensors of other in-vivo parameters, sensors of various in-vivo substances or compounds, or the like Devices, systems and methods according to some embodiments of the present invention, including for example in-vivo sensing devices, receiving systems and/or display systems, may be similar to embodiments described in U.S. Pat. No. 5,604,531 to Iddan et al., entitled "In-vivo Video Camera System", and/or in U.S. Pat. No. 7,009,634 to Iddan et al., entitled "Device for In-Vivo Imaging", and/or in U.S. patent application Ser. No. 10/046,541, entitled "System and Method for Wide Field Imaging of Body Lumens", filed on Jan. 16, 2002, published on Aug. 15, 2002 as U.S. Patent Application Publication Number 2002/0109774, and/or in U.S. patent application Ser. No. 10/046,540, entitled "System and Method for Determining In-vivo Body Lumen Conditions", filed on Jan. 16, 2002, published on Aug. 15, 2002 as U.S. Patent Application Publication Number 2002/0111544, and/or U.S. patent application Ser. No. 10/097,096, entitled "Method and System for Detecting Colorimetric Abnormalities n Vivo", filed on Mar. 14, 2002, published on Nov. 28, 2002 as U.S. Patent Application Publication Number 2002/0177779, all of which are hereby incorporated by reference in their entirety. Devices and systems as described herein may have other configurations and/or sets of components. For example, an external receiver/recorder unit, a processor and a monitor, e.g., in a workstation, such as those described in the above publications, may be suitable for use with some embodiments of the present invention. Devices and systems as described herein may have other configurations and/or other sets of components. For example, the present invention may be practiced using an endoscope, needle, stent, catheter, etc. Some in-vivo devices may be capsule shaped, or may have other shapes, for example, a peanut shape or tubular, spherical, conical, or other suitable shapes.

Some embodiments of the present invention may include, for example, a typically swallowable in-vivo device. In other embodiments, an in-vivo device need not be swallowable and/or autonomous, and may have other shapes or configurations. Some embodiments may be used in various body lumens, for example, the GI tract, blood vessels, the urinary tract, the reproductive tract, or the like. In some embodiments, the in-vivo device may optionally include a sensor, an imager, and/or other suitable components.

Embodiments of the in-vivo device are typically autonomous and are typically self-contained. For example, the in-vivo device may be or may include a capsule or other unit where all the components are substantially contained within a container, housing or shell, and where the in-vivo device does not require any wires or cables to, for example, receive power or transmit information. The in-vivo device may communicate with an external receiving and display system to provide display of data, control, or other functions. For example, power may be provided by an internal battery or an internal power source, or using a wired or wireless power-receiving system. Other embodiments may have other configurations and capabilities. For example, components may be distributed over multiple sites or units; and control information or other information may be received from an external source.

Devices, systems and methods in accordance with some embodiments of the invention may be used, for example, in conjunction with a device which may be inserted into a human body or swallowed by a person. However, embodiments of the invention are not limited in this regard, and may be used, for example, in conjunction with a device which may be inserted into, or swallowed by, a non-human body or an animal body.

Figure 1:
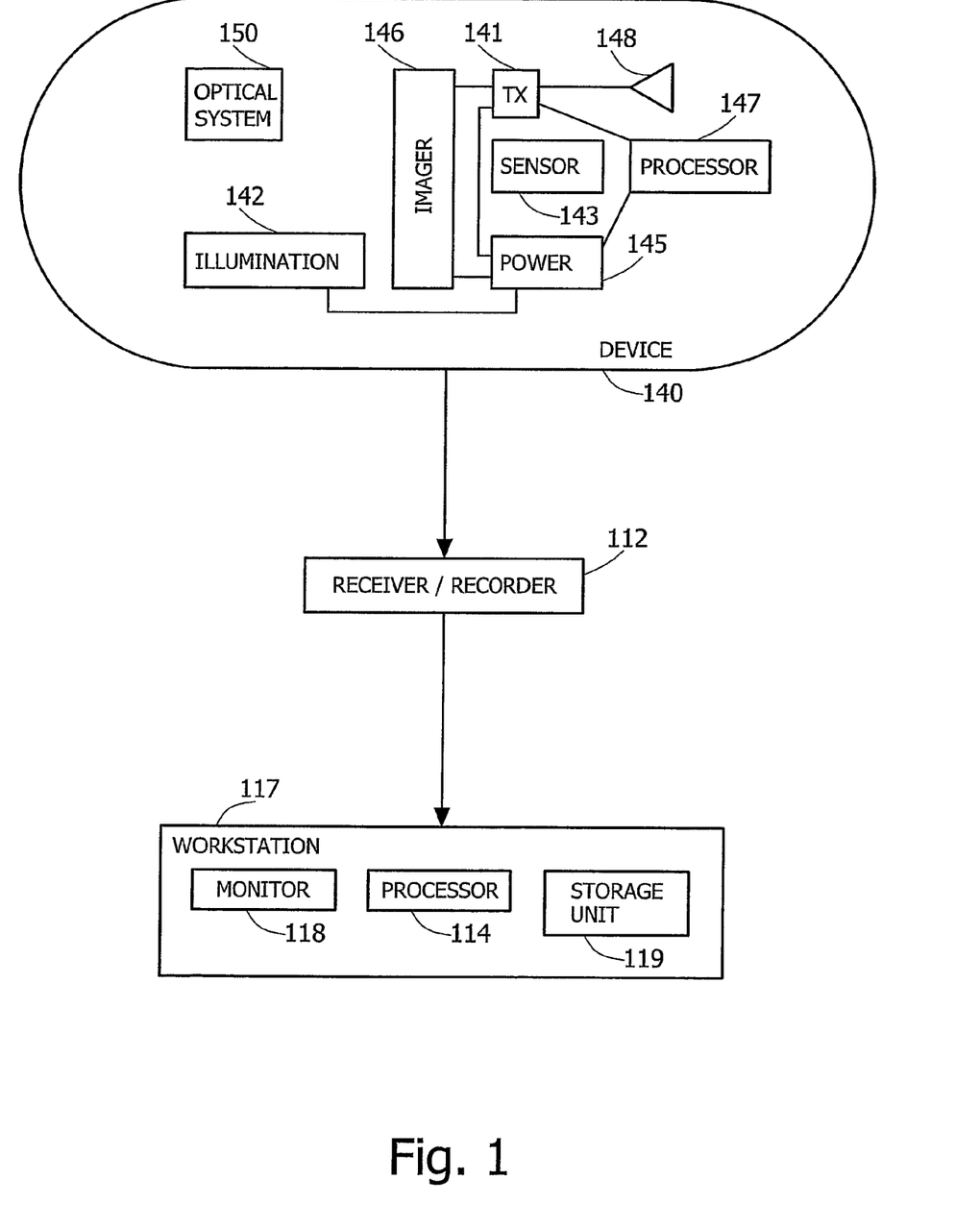
FIG. 1 is a schematic illustration of an in-vivo system according to an embodiment of the invention.

FIG. 1 schematically illustrates an in-vivo system in accordance with some embodiments of the present invention. One or more components of the system may be used in conjunction with, or may be operatively associated with, the devices and/or components described herein or other in-vivo devices in accordance with embodiments of the invention.

In some embodiments, the system may include a device 140 having a sensor, e.g., an imager 146, one or more illumination sources 142, a power source 145, and a transmitter 141. In some embodiments, device 140 may be implemented using a swallowable capsule, but other sorts of devices or suitable implementations may be used. Outside a patient's body may be, for example, an external receiver/recorder 112 (including, or operatively associated with, for example, one or more antennas, or an antenna array), a storage unit 119 which may be or include for example one or more of a memory, a database, etc. or other storage systems, a processor 114, and a monitor 118. In some embodiments, for example, processor 114, storage unit 119 and/or monitor 118 may be implemented as a workstation 117, e.g., a computer or a computing platform.

Transmitter 141 may operate using radio waves; but in some embodiments, such as those where device 140 is or is included within an endoscope, transmitter 141 may transmit/receive data via, for example, wire, optical fiber and/or other suitable methods. Other known wireless methods of transmission may be used. Transmitter 141 may include, for example, a transmitter module or sub-unit and a receiver module or sub-unit, or an integrated transceiver or transmitter-receiver.

Device 140 typically may be or may include an autonomous swallowable capsule, but device 140 may have other shapes and need not be swallowable or autonomous. Embodiments of device 140 are typically autonomous, and are typically self-contained. For example, device 140 may be a capsule or other unit where all the components are substantially contained within a container or shell, and where device 140 does not require any wires or cables to, for example, receive power or transmit information. In some embodiments, device 140 may be autonomous and non-remote-controllable; in another embodiment, device 140 may be partially or entirely remote-controllable.

In some embodiments, device 140 may communicate with an external receiving and display system (e.g., workstation 117 or monitor 118) to provide display of data, control, or other functions. For example, power may be provided to device 140 using an internal battery, an internal power source, or a wireless system able to receive power. Other embodiments may have other configurations and capabilities. For example, components may be distributed over multiple sites or units, and control information or other information may be received from an external source.

In some embodiments, device 140 may include an in-vivo video camera, for example, imager 146, which may capture and transmit images of, for example, the GI tract while device 140 passes through the GI lumen. Other lumens and/or body cavities may be imaged and/or sensed by device 140. In some embodiments, imager 146 may include, for example, a Charge Coupled Device (CCD) camera or imager, a Complementary Metal Oxide Semiconductor (CMOS) camera or imager, a digital camera, a stills camera, a video camera, or other suitable imagers, cameras, or image acquisition components.

In some embodiments, imager 146 in device 140 may be operationally connected to transmitter 141. Transmitter 141 may transmit images to, for example, external transceiver or receiver/recorder 112 (e.g., through one or more antennas), which may send the data to processor 114 and/or to storage unit 119. Transmitter 141 may also include control capability, although control capability may be included in a separate component, e.g., processor 147. Transmitter 141 may include any suitable transmitter able to transmit image data, other sensed data, and/or other data (e.g., control data) to a receiving device. Transmitter 141 may also be capable of receiving signals/commands, for example from an external transceiver. For example, in some embodiments, transmitter 141 may include an ultra low power Radio Frequency (RF) high bandwidth transmitter, possibly provided in Chip Scale Package (CSP).

In some embodiments, transmitter 141 may transmit/receive via antenna 148. Transmitter 141 and/or another unit in device 140, e.g., a controller or processor 147, may include control capability, for example, one or more control modules, processing module, circuitry and/or functionality for controlling device 140, for controlling the operational mode or settings of device 140, and/or for performing control operations or processing operations within device 140. According to some embodiments, transmitter 141 may include a receiver which may receive signals (e.g., from outside the patient's body), for example, through antenna 148 or through a different antenna or receiving element. According to some embodiments, signals or data may be received by a separate receiving device in device 140.

Power source 145 may include one or more batteries or power cells. For example, power source 145 may include silver oxide batteries, lithium batteries, other suitable electrochemical cells having a high energy density, or the like. Other suitable power sources may be used. For example, power source 145 may receive power or energy from an external power source (e.g., an electromagnetic field generator), which may be used to transmit power or energy to in-vivo device 140.

In some embodiments, power source 145 may be internal to device 140, and/or may not require coupling to an external power source, e.g., to receive power. Power source 145 may provide power to one or more components of device 140 continuously, substantially continuously, or in a non-discrete manner or timing, or in a periodic manner, an intermittent manner, or an otherwise non-continuous manner. In some embodiments, power source 145 may provide power to one or more components of device 140, for example, not necessarily upon-demand, or not necessarily upon a triggering event or an external activation or external excitement.

Optionally, in some embodiments, transmitter 141 may include a processing unit or processor or controller, for example, to process signals and/or data generated by imager 146. In another embodiment, the processing unit may be implemented using a separate component within device 140, e.g., controller or processor 147, or may be implemented as an integral part of imager 146, transmitter 141, or another component, or may not be needed. The processing unit may include, for example, a Central Processing Unit (CPU), a Digital Signal Processor (DSP), a microprocessor, a controller, a chip, a microchip, a controller, circuitry, an Integrated Circuit (IC), an Application-Specific Integrated Circuit (ASIC), or any other suitable multi-purpose or specific processor, controller, circuitry or circuit. In some embodiments, for example, the processing unit or controller may be embedded in or integrated with transmitter 141, and may be implemented, for example, using an ASIC.

Processor 114 may include a processing unit, processor or controller. The processing unit may include, for example, a CPU, a DSP, a microprocessor, a controller, a chip, a microchip, a controller, circuitry, an IC, an ASIC, or any other suitable multi-purpose or specific processor, controller, circuitry or circuit.

In some embodiments, imager 146 may acquire in-vivo images continuously, substantially continuously, or in a non-discrete manner, for example, not necessarily upon-demand, or not necessarily upon a triggering event or an external activation or external excitement; or in a periodic manner, an intermittent manner, or an otherwise non-continuous manner.

In some embodiments, transmitter 141 may transmit image data continuously, or substantially continuously, for example, not necessarily upon-demand, or not necessarily upon a triggering event or an external activation or external excitement; or in a periodic manner, an intermittent manner, or an otherwise non-continuous manner.

In some embodiments, device 140 may include one or more illumination sources 142, for example one or more Light Emitting Diodes (LEDs), "white LEDs", or other suitable light sources. Illumination sources 142 may, for example, illuminate a body lumen or cavity being imaged and/or sensed. An optional optical system 150, including, for example, one or more optical elements, such as one or more lenses or composite lens assemblies, one or more suitable optical filters, or any other suitable optical elements, may optionally be included in device 140 and may aid in focusing reflected light onto imager 146, focusing illuminated light, and/or performing other light processing operations.

In some embodiments, illumination source(s) 142 may illuminate continuously, or substantially continuously, for example, not necessarily upon-demand, or not necessarily upon a triggering event or an external activation or external excitement. In some embodiments, for example, illumination source(s) 142 may illuminate a pre-defined number of times per second (e.g., two or four times), substantially continuously, e.g., for a time period of two hours, four hours, eight hours, or the like; or in a periodic manner, an intermittent manner, or an otherwise non-continuous manner.

In some embodiments, the components of device 140 may be enclosed within a housing or shell, e.g., capsule-shaped, oval, or having other suitable shapes. The housing or shell may be substantially transparent or semi-transparent, and/or may include one or more portions, windows or domes that may be substantially transparent or semi-transparent. For example, one or more illumination source(s) 142 within device 140 may illuminate a body lumen through a transparent or semi-transparent portion, window or dome; and light reflected from the body lumen may enter the device 140, for example, through the same transparent or semitransparent portion, window or dome, or, optionally, through another transparent or semi-transparent portion, window or dome, and may be received by optical system 150 and/or imager 146. In some embodiments, for example, optical system 150 and/or imager 146 may receive light, reflected from a body lumen, through the same window or dome through which illumination source(s) 142 illuminate the body lumen.

Data processor 114 may analyze the data received via external receiver/recorder 112 from device 140, and may be in communication with storage unit 119, e.g., transferring frame data to and from storage unit 119. Data processor 114 may provide the analyzed data to monitor 118, where a user (e.g., a physician) may view or otherwise use the data. In some embodiments, data processor 114 may be configured for real time processing and/or for post processing to be performed and/or viewed at a later time. In the case that control capability (e.g., delay, timing, etc) is external to device 140, a suitable external device (such as, for example, data processor 114 or external receiver/recorder 112 having a transmitter or transceiver) may transmit one or more control signals to device 140.

Monitor 118 may include, for example, one or more screens, monitors, or suitable display units. Monitor 118, for example, may display one or more images or a stream of images captured and/or transmitted by device 140, e.g., images of the GI tract or of other imaged body lumen or cavity. Additionally or alternatively, monitor 118 may display, for example, control data, location or position data (e.g., data describing or indicating the location or the relative location of device 140), orientation data, and various other suitable data. In some embodiments, for example, both an image and its position (e.g., relative to the body lumen being imaged) or location may be presented using monitor 118 and/or may be stored using storage unit 119. Other systems and methods of storing and/or displaying collected image data and/or other data may be used.

Typically, device 140 may transmit image information in discrete portions. Each portion may typically correspond to an image or a frame; other suitable transmission methods may be used. For example, in some embodiments, device 140 may capture and/or acquire an image once every half second, and may transmit the image data to external receiver/recorder 112. Other constant and/or variable capture rates and/or transmission rates may be used.

Optionally, device 140 may include one or more sensors 143, instead of or in addition to a sensor such as imager 146. Sensor 143 may, for example, sense, detect, determine and/or measure one or more values of properties or characteristics of the surrounding of device 140. For example, sensor 143 may include a pH sensor, a temperature sensor, an electrical conductivity sensor, a pressure sensor, or any other known suitable in-vivo sensor.

Some embodiments of the invention may automatically identify, or may determine a presence of, a varix, multiple varices, or one or more varicose veins. Other vessels may be identified, for example, dilated veins, abnormal veins, veins having blue or blue-like color, arteries, lymph vessels, enlarged veins, twisted veins, painful veins, superficial veins resulting from poorly functioning valves, or the like. Veins or varices may be identified, for example, in the GI tract, in a wall or walls of the GI tract, in the esophagus or walls thereof, in the lower portion of the esophagus or walls thereof, in the upper part of the stomach, in the stomach or in walls thereof, in proximity to the GI tract, or in other areas.

In some embodiments, for example, image analysis and/or image comparison may be performed, for example, to determine that an in-vivo image acquired by device 140 includes at least a portion which corresponds to or indicates a varix or a vein. The image analysis or image comparison may be performed, for example, in-vivo (e.g., by processor 147 of device 140), or may be performed ex-vivo (e.g., by processor 114 of workstation 117, or by a processor or controller which may optionally be included in receiver/recorder 112).

In some embodiments, the image analysis and/or comparison may be performed in substantially real time, for example, while device 140 is in-vivo, while imager 146 acquires images, while transmitter 141 transmits image data, while receiver/recorder 112 receives image data, and/or while workstation 117 displays in-vivo images. In other embodiments, the image analysis and/or comparison may include, for example pre-processing operations (e.g., performed prior to presentation of an in-vivo image stream or a portion thereof) or post-processing operations (e.g., performed after presentation of an in-vivo image steam or a portion thereof), and may optionally result in the selective presentation of indication of selected in-vivo images (or selected portions of the in-vivo image stream) which correspond to or include varices or veins.

In some embodiments, the image analysis or image comparison may include, for example, identification or determination of one or more signs indicating the existence or presence of a varix or a vein. In some embodiments, for example, a varix or vein may be identified based on a ridge-like protrusion of the varix or vein, or based on a pre-defined shape (e.g., circular, round, oval, semi-circular, or other morphology) or pattern associated with varices or veins, and/or based on one or more colors associated with varices or veins. In some embodiments, for example, the image analysis or image comparison may include a colorimetric analysis or a color analysis, e.g., identification of blue color or blue-like color of a protrusion into the GI tract being imaged. In some embodiments, for examples, the image analysis may search for a blue protrusion into the imaged GI tract, e.g., which may appear in an image of the esophageal lumen. For example, the blue or bluish protrusion may be attributed to unoxygenated venous blood in the varix, e.g., in contrast to the red blood in an artery. Some embodiments may search for and identify a blue-like color and/or a vein-like structure or pattern in an in-vivo image frame.

Upon identification of a varix or vein, the in-vivo frame(s) in which the varix or vein are identified may be marked or tagged, e.g., for further inspection by a user (e.g., a physician). In some embodiments, an indication (e.g., an alert message, an audible sound, or the like) may be used to alert the attention of the user to the identified varix or vein, and/or to otherwise indicate to the user the determination of varices or veins.

In some embodiments, a stream of images captured and/or transmitted by device 140 may be stored in for example storage unit 119, and each image analyzed for varices or other features. Individual images, or portions of the image stream, may be marked as possibly including varices.

Figure 2A:
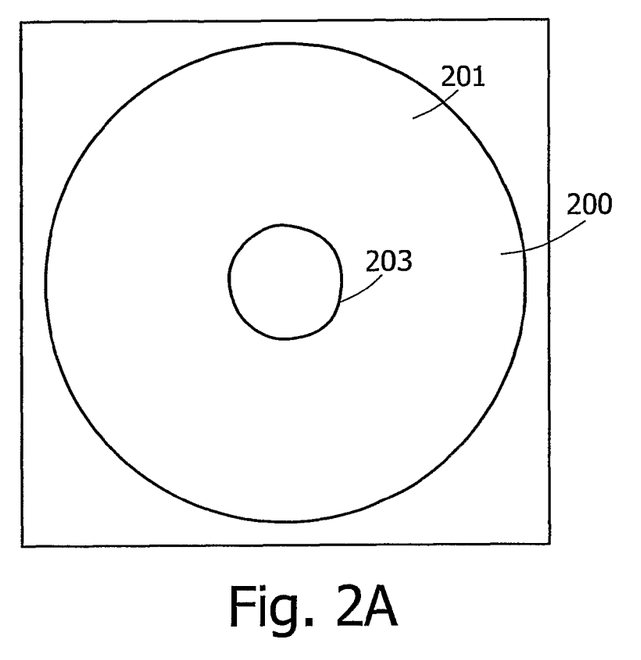
FIGS. 2A and 2B are schematic illustrations of demonstrative in-vivo images showing a healthy lumen wall and a lumen wall with a varix in accordance with an embodiment of the invention.
Figure 2B:
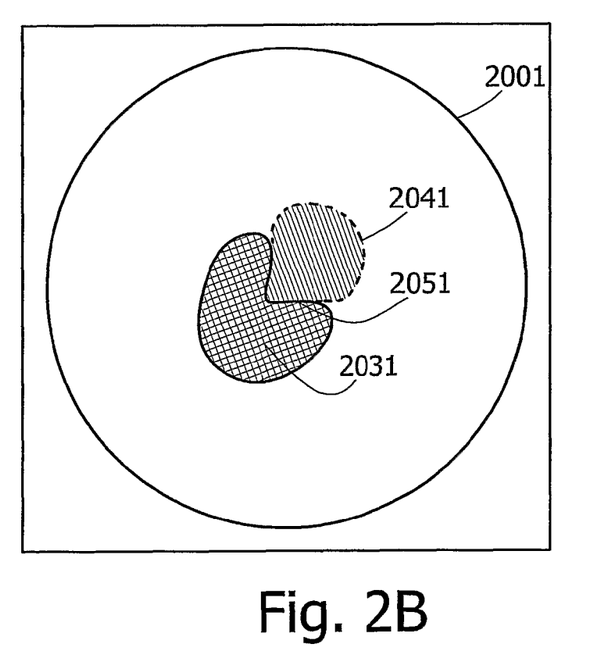

FIG. 2A is a schematic illustration of a demonstrative in-vivo image 200 of a healthy esophageal lumen wall and FIG. 2B is a schematic illustration of a demonstrative in vivo image 2001 of esophageal lumen wall with a varix both of which may be acquired and analyzed in accordance with some embodiments of the present invention. In-vivo image 200 may include, for example, a ring like portion 201 which may correspond to an image body lumen wall, e.g., the GI tract and a circular portion 203 may correspond to the lumen. The ring-shaped portion 201 may typically have, for example, a red color, a pink color, a brown color, or a combination of red, pink and brown and/or other colors. The central portion 203 may have, for example, a black color or a dark color, and may correspond to the lumen that may be opened or partially opened. Alternatively, when the lumen may be closed, the circular portion 203 may not be present and the lumen wall may fill in the circular area 203. Typically closure of the lumen may be accompanied by symmetrical folds around a central point due to muscle contraction, e.g. forming a star like pattern. The folds may be folds of lumen wall tissue and may typically include a red color, a pink color, a brown color, or a combination of red, pink and brown and/or other colors.

Reference is now made to FIG. 2B showing a schematic illustration of a demonstrative in vivo image 2001 of an esophageal lumen wall with a varix according to an embodiment of the present invention. In FIG. 2B ring like portion 2001 may include, for example, varix 2041 that may include a bluish area and/or a protruding area 2051 that may protrude into the lumen 2031. In some examples the varix 2041 may include reddish spots. Typically the varix may protrude into the lumen 2031 so that the lumen may be distorted from its normally substantially circular shape. For example, the lumen may include a convex shaped portion outlined by protrusion 2051. Alternatively, while the lumen is closed, e.g. during a contraction, a closure including a varix may be depicted by the asymmetry or lack of symmetry in the closure. For example, the folds typically seen when capturing images of a closed lumen may be asymmetric, e.g. a distorted star-like pattern. In one example, the area of the varix may not include folds.

As shown in FIG. 2B, in-vivo image 2001 may include a protrusion 2041. In some embodiments, for example, protrusion 2041 may have a color associated with a varix or a vein or a dilated vein, e.g., a blue or blue-like color. For example an edge may be detectable around and/or in the vicinity of the bluish area. In some embodiments, optionally, the contour of protrusion 2041 may include an arch 2051 protruding into the lumen 2031. Other suitable patterns, shapes or morphologies may be used.

Some embodiments of the invention may include, for example, a method for detecting one or more varices, veins, varicose veins, dilated veins, or other vessels of interest. The method may include, for example, performing image analysis and/or image comparison to identify, in one or more in-vivo images or in an in-vivo image stream, one or more properties associated with varices, veins, varicose veins, dilated veins, or other vessels of interest. The analysis may include, for example, determination or identification of a protrusion, a blue or blue like image portion, and/or a blue or blue-like protrusion. In some embodiments, in-vivo image frames in which varices or veins are identified, may be marked or tagged, may be presented (e.g., selectively or separately) to a user, may be brought to the user's attention using a visual or audible indication, or may be otherwise further presented, processed or handled.

Figure 3:
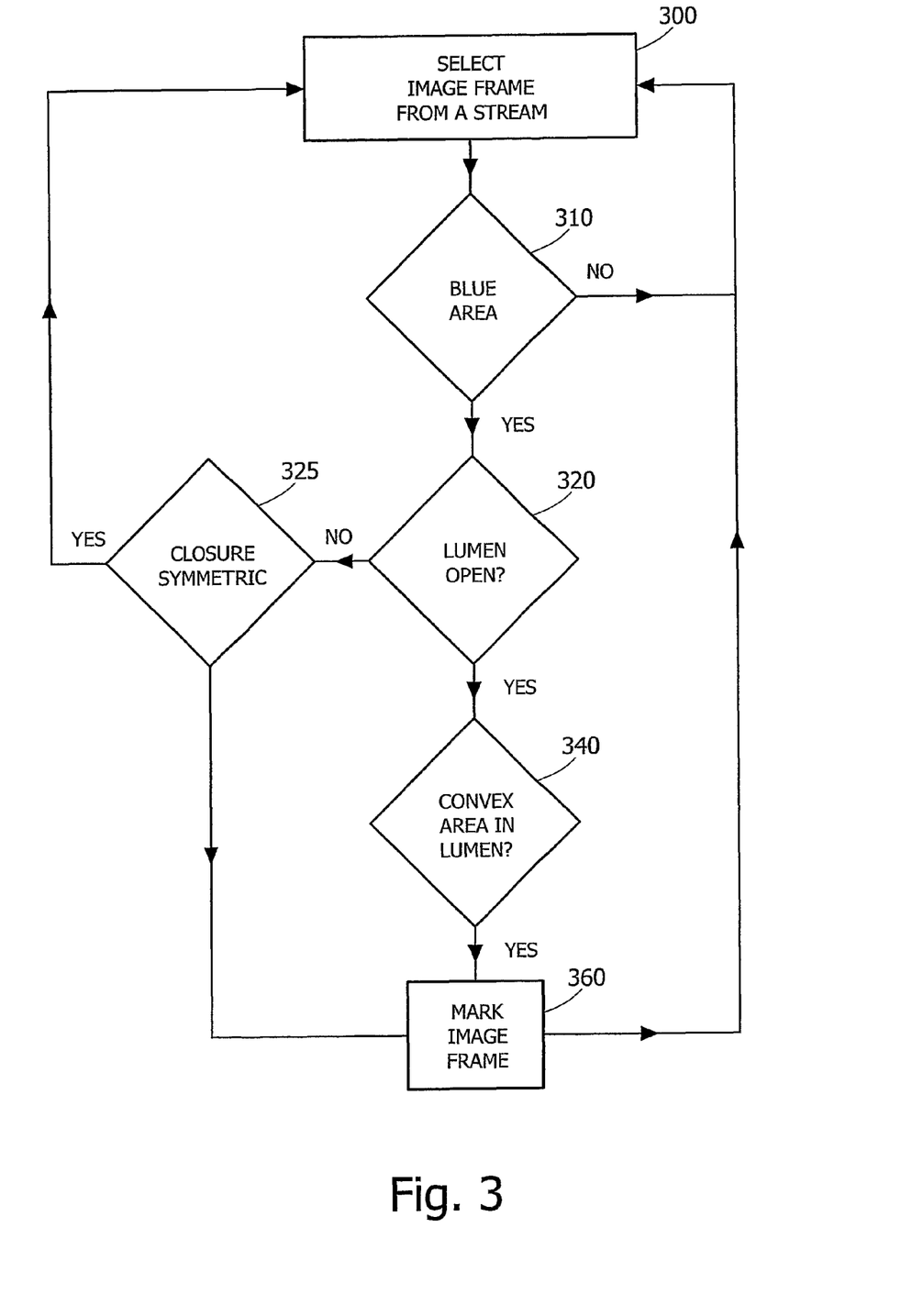
FIG. 3 is a flowchart depicting a sample method for automatic detection of varices on a body lumen wall according to embodiments of the present invention.

Reference is now made to FIG. 3 describing a sample method for automatically detecting image frames displaying a varix according to embodiments of the present invention. In block 300 an image frame from a stream of image frames captured within a body lumen may be selected for varix detection. In some embodiments of the present invention, image frames captured in a specific area of the GI tract, e.g. the esophagus may each be inspected for varices. Each image selected may be inspected for the presence of a blue and/or substantially blue area. In other embodiments each image within an image stream may be scanned for varices. Automatic inspection of color may performed by methods known in the art. In decision block 310 a process may decide if a blue area was detected. In some examples edge detection may be performed around an identified blue area to detect if the blue area is a protruding blue area as is typical for varices. The presence of an edge around a blue area may strengthen the decision that the blue area may indicate varices. In decision block 320 the status of the lumen is inspected for either an open and/or closed state. When the lumen is open, a protrusion of the lumen wall into the lumen area may be detected. For example, a lumen area may be inspected for a convex area. Methods known in the art to detect convex shaped edges may be implemented. An image frame including a substantially blue area with a convex shaped lumen may be selected as an image that may show varices. In block 360 such an image may be marked for display or tagging during a display of a stream of images. Once marked and/or displayed a subsequent image frame may be inspected.

For image frames captured during a contraction, an image frame may be inspected for asymmetries in the closure of the lumen. Asymmetries in the closure of the lumen may be indicative of the presence of a varix. For examples, when imaging a lumen from within the lumen for healthy patients typically the closure may be seen to be accompanied by a star like pattern surrounding a central point of the lumen that may result from folds of the muscle walls to close the lumen. A varix protrusion may distort the typically star like pattern. A decision may be made in decision block 325 regarding the symmetry of the closure. An image frame with a detected bluish area and an asymmetric closure of the lumen may be indicative of the presence of a varix and may be marked for further inspection by a health professional. In some examples red spots in the vicinity of a bluish area may be an indication of the presence of varices. Other steps or methods may be used to detect the presence of varices in an image frame captured within a body lumen.

In some embodiments, optionally, one or more of the operations described herein may be performed automatically, e.g., by the system of FIG. 1. In some embodiments, optionally, a medical diagnosis or a determination of a pathology may be generated, e.g., substantially automatically, based on the automatic detection of varices or veins.

Figure 4:
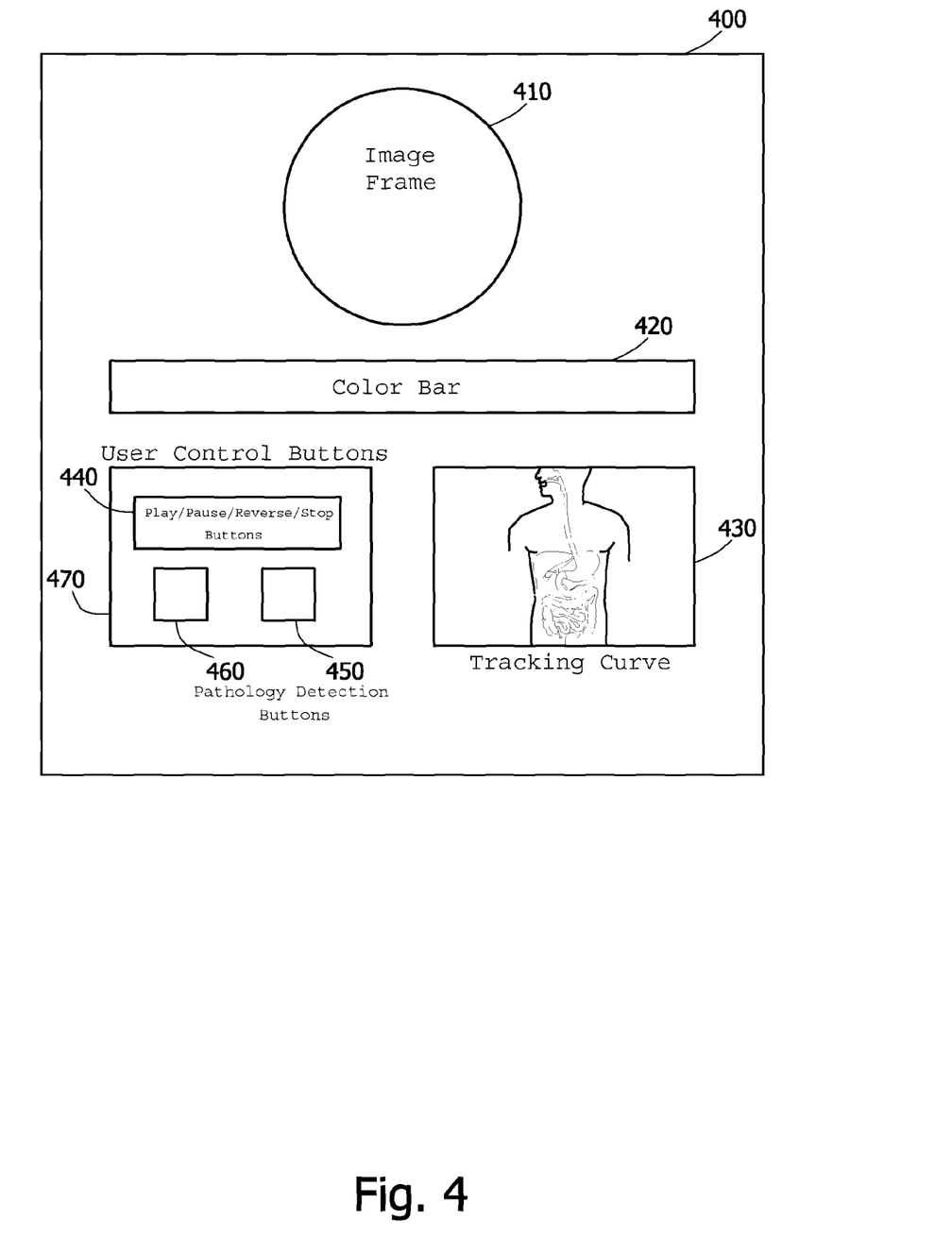
FIG. 4 is a sample graphical user interface (GUI) for varices detection according to embodiments of the present invention.

Reference is now made to FIG. 4 showing a sample GUI for varices detection according to embodiments of the present invention. In some embodiments, the GUI display 400 may include presentation of an image frame 410, e.g. a streaming presentation image frames and/or movie captured within the body lumen, a color bar 420 or other summary bar or window summarizing the information in the movie with color, a tracking curve 430 indicating where the imaging device captured the presented image frame, and user control buttons 470. Other functions and or displays may be included within the GUI presentation 400. In some embodiments, user control buttons may include play/pause/reverse/stop buttons 440 to control the display of the image frames 410. In addition, one or more pathology detection buttons 460 and 470 may also be included. For example, button 460 may initiate varices detection as may be described herein. For example, upon activating the varices detector button 460, varices detection may be performed and only image frames potentially showing varices may be screened in image display 410. In other examples, marks along the color bar 420 may indicate where along the image stream potential varices may be present. In yet other examples, markings on the tracking curve 430 may indicate positions along the body lumen where varices may be present based on the automatic detection described herein. Color bar 420 may be similar to embodiments described in U.S. Patent Publication Number US20050075551 published on Apr. 7, 2005 and entitled "System and method for presentation of data streams" which is hereby incorporated by reference in its entirety.

According to some embodiments of the present invention, the method described herein for varices detection may be performed in real time while in-vivo device 140 may be capturing images in-vivo and transmitting them to a receiver/recorder 112. According to other embodiments, varices detection may be performed off-line after collection and downloading of all and/or a portion of the image frames captured and received by receiver/recorder 112 and/or workstation 117.

Various aspects of the various embodiments disclosed herein are combinable with the other embodiments disclosed herein.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:

1. A system for automatic analysis of in-vivo images comprising:
    an in-vivo imaging device to acquire an in-vivo image of a body lumen;
    a memory to store the in-vivo image; and
    a processor to detect a varix, said detection performed by automatically identifying, in the in-vivo image, a protrusion into the lumen, wherein at least part of the protrusion is substantially blue, identifying a closed lumen in the in-vivo image, and identifying asymmetries in the closure of the lumen.

2. The system of claim 1, wherein the protrusion comprises at least part of a circular pattern enclosed within at least part of the wall of the imaged lumen.

3. The system of claim 1, wherein the body lumen is a gastro-intestinal tract or a portion thereof.

4. The system of claim 1, wherein the processor is to generate an indication that the in-vivo image includes a varix.

5. The system of claim 1, wherein the in-vivo imaging device comprises a swallowable capsule.

6. A method for automatic analysis of in-vivo images comprising:

receiving an in-vivo image of a gastro-intestinal tract; and processing the in-vivo image to detect a varix, said processing performed by automatically identifying a protrusion into a lumen of the gastro-intestinal tract, wherein at least part of the protrusion is substantially blue, identifying a closed lumen in the in-vivo image, and identifying asymmetries in the closure of the lumen.

7. The method of claim 6, further comprising detecting an edge around the substantially blue part of the protrusion.

8. The method of claim 6, further comprising providing a user interface to initiate the varix detection.

9. The method of claim 8, wherein the user interface comprises one or more pathology detection buttons.

10. The method of claim 6, wherein the protrusion comprises at least part of a circular pattern enclosed within at least part of the wall of the imaged lumen.

11. The method of claim 6, further comprising displaying an indication that the in-vivo image includes a varix.

12. The method of claim 6, further comprising displaying the in-vivo image.

13. A method for automatically detecting image frames displaying a varix, the method comprising:

selecting an in-vivo image frame from a stream of images captured within a body lumen;

processing the in-vivo image frame to detect the presence of a blue and/or substantially blue area;

processing the in-vivo image to detect the presence of an edge of said blue and/or substantially blue area protruding into said body lumen;

processing the in-vivo image to determine the status of said body lumen as either in an open or closed state; and marking an in-vivo image having a blue and/or substantially blue area protruding into said body lumen, wherein said body lumen is in an open state.

\* \* \* \* \*